United States Patent [19]

Moynihan

[11] Patent Number: 5,589,189
[45] Date of Patent: Dec. 31, 1996

[54] LIPOSOME DISPERSION

[75] Inventor: Karen L. Moynihan, Brea, Calif.

[73] Assignee: NeXstar Pharmaceuticals, Inc., Boulder, Colo.

[21] Appl. No.: 306,036

[22] Filed: Sep. 14, 1994

[51] Int. Cl.$^6$ .................................................. A61K 9/127
[52] U.S. Cl. .......................... 424/450; 264/4.1; 264/4.3; 264/4.6
[58] Field of Search .................. 424/450; 264/4.1, 264/4.3, 4.6

[56] References Cited

U.S. PATENT DOCUMENTS

| | | | |
|---|---|---|---|
| 4,133,874 | 1/1979 | Miller et al. | 424/450 |
| 4,229,360 | 10/1980 | Schneider et al. | 260/403 |
| 4,532,130 | 7/1985 | Djordjevich | 424/450 |
| 4,636,479 | 1/1987 | Martin | 436/533 |
| 4,746,516 | 5/1988 | Moro et al. | 424/450 |
| 4,753,788 | 6/1988 | Gamble | 424/1.1 |
| 4,776,991 | 10/1988 | Farmer et al. | 264/4.3 |
| 4,814,270 | 3/1989 | Piran | 264/4.3 |
| 4,911,929 | 3/1990 | Farmer et al. | 424/450 |
| 4,963,297 | 10/1990 | Madden | 264/4.3 |
| 5,000,887 | 3/1991 | Tenzel | 264/4.6 |
| 5,094,785 | 3/1992 | Law | 264/4.3 |
| 5,340,587 | 8/1994 | Mihalko | 424/450 |

FOREIGN PATENT DOCUMENTS

| | | |
|---|---|---|
| WO90/03795 | 4/1990 | WIPO . |
| WO90/11781 | 10/1990 | WIPO . |
| WO92/01068 | 1/1992 | WIPO . |
| WO92/10203 | 6/1992 | WIPO . |

OTHER PUBLICATIONS

Beissinger, Trans Am. Soc. Artif. Intern organs, vol. XXXII, p. 58 1986.

Farmer, Martha et al., Liposome–Encapsulated Hemoglobin as an Artificial Oxygen–Carrying System. *Methods in Enzymology*, vol. 149: 184, 184–194.

Rudolph, A. S., Encapsulated Hemoglobin: Current Issues and Future Goals. *Art. Cells Blood Subs., and Immob. Biotech.* (1994) 22(2):354–356.

*Primary Examiner*—Gollamudi S. Kishore
*Attorney, Agent, or Firm*—Adam Cochran; David S. Bradin

[57] ABSTRACT

A process for the production of a non-aggregating, filterable dispersion of liposomal encapsulated hemoglobin includes the addition of a plasma protein such as human serum albumin to a liposome dispersion and the application of liposome-forming energy to the dispersion sufficient to form unilamellar vesicles having a diameter smaller than 0.2 μm.

4 Claims, No Drawings

LIPOSOME DISPERSION

The U.S. Government has rights in this invention pursuant to Contract No. N00014-93-C-2192 awarded by Naval Reasearch Laboratory.

FIELD OF THE INVENTION

This invention relates to blood substitutes, and more particularly to a method for the large scale production of a filterable oxygen-carrying fluid that can be administered to patients as a blood substitute by transfusion.

BACKGROUND OF THE INVENTION

The transfusion of red blood cells is the primary method presently available for providing blood to patients experiencing hemorrhage or undergoing invasive medical procedures such as surgery. However, the use of blood presents problems for both healthcare workers and patients. For example, blood products require special storage conditions (i.e., freezing temperature) which can impose a short shelf life, and therefore large amounts of stored blood are discarded. Blood shortages occur because the supply from donors is not always assured. Blood transfusion requires properly matched blood types to avoid antigenic response, and also presents the possibility of contamination by blood born pathogens such as the human immunodeficiency virus. Thus, a search for blood substitutes has been undertaken in order to provide an alternative to blood transfusion.

Free hemoglobin solutions have been investigated as potential blood substitute products because workers would not have to be concerned with antigenic response (which is caused by non-hemoglobin blood factors) and because it might be easier to store and have a longer shelf life. However, it is known that free hemoglobin converts from its natural tetrameric form to a dimeric form that is rapidly excreted by the kidney. Renal toxicity has also been observed. Further, stroma free (cell free) hemoglobin is known to have a low $P_{50}$ and high oxygen binding affinity (and therefore slow release) because of the absence of 2,3-diphosphoglycerate. Thus, efforts to overcome these problems have been directed toward developing a modified hemoglobin product, or some form of synthetic red blood cell.

In an attempt to overcome problems associated with the use of cell-free hemoglobin solutions, many have sought to create a synthetic red blood cell with hemoglobin encapsulated therein. For example, liposome encapsulated hemoglobin formulations and methods for making them are known in the art: U.S. Pat. Nos. 4,776,991 and 4,911,929 (Farmer), 4,532,130 (Djordjevich) and 4,133,874 (Miller); the disclosures of which are incorporated by reference herein.

Liposomes are microscopic vesicles made from phospholipids, which form closed, fluid filled spheres when dispersed with aqueous solutions. Phospholipid molecules are polar, having a hydrophilic head and two hydrophobic tails consisting of long fatty acid chains. Thus, when a sufficient concentration of phospholipid molecules are present in aqueous solutions, the mils spontaneously associate to exclude water while the hydrophilic phosphate heads interact with water. The result is a spherical, bilayer membrane in which the fatty acid tails converge in the interior of the newly formed membrane, and the polar heads point in opposite directions toward an aqueous medium. These bilayer membranes thus form closed, hollow spheres known as liposomes. The polar heads at the inner surface of the membrane point toward the aqueous interior of the liposome and, at the opposite surface of the spherical membrane, the polar heads interact with the surrounding aqueous medium. As the liposomes are formed, water soluble molecules can be incorporated into the aqueous interior, and lipophilic molecules may be incorporated into the lipid bilayer. Liposomes may be either multilamellar, like an onion with liquid separating many lipid bilayers, or unilamellar, with a single bilayer surrounding an aqueous center.

Methods for producing liposomes are well known in the art, and there are many types of liposome preparation techniques which may be employed to produce various types of liposomes. These can be selected depending on the use, the chemical intended to be entrapped, and the type of lipids used to form the bilayer membrane. The requirements which must be considered in producing a liposome preparation are similar to those of other controlled release mechanisms. They are: (1) a high percent of chemical entrapment; (2) increased chemical stability; (3) low drug toxicity; (4) rapid method of production; and (5) a reproducible size distribution.

The first method described to encapsulate drugs or other chemicals in liposomes involved the production of multilamellar vesicles (MLVs). Liposomes can also be formed as unilamellar vesicles (UVs), which generally have a size less than 0.5 µm (µm, also referred to as "microns"). There are several techniques known in the art which are used to produce unilamellar liposomes.

Smaller unilamellar vesicles can be formed using a variety of techniques, such as applying a force sufficient to reduce the size of the liposomes and or produce smaller unilamellar vesicles. Such force can be produced by a variety of methods, including homogenization, sonication or extrusion (through filters) of MLVs. These methods results in dispersions of UVs having diameters of up to 0.2 µm, which appear as clear or translucent suspensions. Other standard methods for the formation of liposomes are known in the art, for example, methods for the commercial production of liposomes include the homogenization procedure described in U.S. Pat. No. 4,753,788 to Gamble, a preferred technique, and the method described in U.S. Pat. No. 4,935,171 to Bracken, which are incorporated herein by reference.

Another method of making unilamellar vesicles is to dissolve phospholipids in ethanol and inject them into a buffer, whereby the lipids will spontaneously rearrange into unilamellar vesicles. This provides a simple method to produce UVs which have internal volumes similar to that of those produced by sonication (0.2–0.5 L/mol of lipid). Another common method for producing small UVs is the detergent removal technique. Phospholipids are solubilized in either ionic or non-ionic detergents such as cholates, Triton X-100, or n-alkylglucosides. The drug is then mixed with the solubilized lipid-detergent micelles. Detergent is then removed by one of several techniques: dialysis, gel filtration, affinity chromatography, centrifugation or ultrafiltration. The size distribution and entrapment efficiencies of the UVs produced this way will vary depending on the details of the technique used.

The therapeutic uses of liposomes include the delivery of drugs which are normally toxic in the free form. In the liposomal form the toxic drug may be directed away from the sensitive tissue and targeted to selected areas. Liposomes can also be used therapeutically to release drugs, over a prolonged period of time, reducing the frequency of administration. In addition, liposomes can provide a method for forming an aqueous dispersion of hydrophobic chugs for intravenous delivery.

When liposomes are used to target encapsulated drugs to selected host tissues, and away from sensitive tissues, several techniques can be employed. These procedures involve manipulating the size of the liposomes, their net surface charge as well as the route of administration. More specific manipulations have included labeling the liposomes with receptors or antibodies for particular sites in the body. The route of delivery of liposomes can also affect their distribution in the body. Passive delivery of liposomes involves the use of various routes of administration, e.g., intravenous, subcutaneous and topical. Each route produces differences in localization of the liposomes. Two methods used to actively direct the liposomes to selected target areas are binding either antibodies or specific receptor ligands to the surface of the liposomes. Antibodies are known to have a high specificity for their corresponding antigen and have been shown to be capable of being bound to the surface of liposomes, thus increasing the target specificity of the liposome encapsulated drug.

Since the chemical composition of many drugs precludes their intravenous administration, liposomes can be very useful in adapting these drugs for intravenous delivery. Furthermore, since liposomes are essentially hollow spheres made up of amphipathic molecules, they can entrap hydrophilic drugs in their aqueous interior space and hydrophobic molecules in their lipid bilayer. Unwanted molecules that remain in the dispersion external to the liposomes, such as unentrapped agents, are removed by column chromatography or ultrafiltration. Although methods for making liposomes are well known in the art; it is not always possible to determine a working formulation without experimentation.

One important characteristic of a regulatory approved parenteral product is that it be sterile. Terminal sterile filtration is preferred to aseptic processing for the generation of a sterile parenteral product, and has been found to be the most effective in terms of processing and liposome stability. The best method for terminal sterile filtration is the sequential filtration of a dispersion of liposomes through a 0.45 and 0.22 micron filtration system, and liposomes larger than 0.2 μm or aggregations of smaller liposomes will obstruct and clog this filter system, as well as the ultrafiltration system employed to remove unentrapped components. The Farmer patents disclose the small scale filtration of a liposome encapsulated hemoglobin formulation dispersed in a hyperosmotic buffered saline solution through a 0.22 micron filter. Similarly, Djordjevich discloses a laboratory process for filtering liposome encapsulated hemoglobin dispersed in a saline solution through a 0.22 micron filter for purposes of sterilization.

Another important aspect of developing a liposome formulation is to achieve a unimodal or controlled particle size distribution of unilamellar liposomes having a median size less then 0.2 μm. Controlling the particle size distribution provides not only for a sterile filterable product but it also provides other numerous processing and pharmacological benefits such as RES avoidance and longer circulation times.

It has been desideratum to provide a process for preparing dispersion of hemoglobin encapsulating unilamellar liposomes that have a unimodal size distribution that do not aggregate, thus are capable of being ultrafiltered and are sterile filterable.

SUMMARY OF THE INVENTION

According to the invention, a method is provided for producing a non-aggregating, filterable dispersion of liposomes comprising forming a solution containing a dispersion of multilamellar liposomes and subjecting the solution to a force sufficient to reduce the size of the lipsomes; and adding a globular, preferably a plasma, protein to the solution during the application of the force. The protein may be added after the beginning of the application of the force, provided that the liposomes are subjected to a further force sufficient to produce a dispersion of unilamellar liposomes. The protein may also be added prior to the initial application of the liposome forming force, provided that the solution to which the protein is added is a low ionic strength aqueous solution or buffer. In this regard, a solution of low ionic strength is defined as a solution having a total ion concentration of less than 5 to 50 mM, preferably from 0.1 to 50 mM. Significant advantages are obtained when the dispersion is essentially free of ions (having essentially no ionic strength), and particularly being essentially free of phosphate ions, during the liposome forming procedure, e.g., during homogenization.

The liposome forming force utilized must be sufficient to produce unilamellar vesicles having a mean diameter of less than 0.2 μm. The resulting liposomes produced have a particle size distribution wherein 85 to 100 percent, by volume, of the liposomes have a median diameter of less than 0.2 μm. The preferred method used to provide a force to reduce the size of the lipsomes is applied through homogenization. However, other applications are available such as sonication and extrusion. Various globular plasma proteins maybe used such as albumin; immunoglobulin; alpha, beta or gamma globulin; α-1 lipoprotein and mixtures thereof. The preferred protein is human serum albumin. A preferred formulation includes incorporating into the liposomes an active agent such as a therapeutic or an imaging agent. The preferred size range of the liposomes is between 0.08 and 0.15 μm, with the median diameter.

Also provided is a process for producing liposome encapsulated hemoglobin comprising: forming a solution including a plasma protein and a dispersion of liposome encapsulated hemoglobin; subjecting the solution to a force sufficient to reduce the median size of the liposomes to less then 0.2 μm wherein the resulting liposomes are unilamellar and have a unimodal particle size distribution, provided that when the protein is added prior to the application of the force the solution comprises an aqueous solution containing less then or equal to 20–40 mM phosphate buffer; and filtering the resulting liposomes through a filter passing particles having a size less then or equal to 0.45 microns. The liposomes can be ultra- or sterile filtered in the absence of a hyperosmotic buffered saline and in the presence of sucrose. The process also results in a liposome formulation that is suitable for lyophilization.

Also provided is a process for producing liposomes, that includes forming a solution including a plasma protein and a dispersion of liposomes; then subjecting the solution to a force sufficient to reduce the median size of the liposomes to less then 0.2 μm wherein the resulting liposomes are unilamellar and have a unimodal particle size distribution; and filtering the resulting liposomes through a filter having a size less then or equal to 0.45 microns. More specifically, a process is provided for producing a liposome encapsulated hemoglobin comprising: (a) forming a solution including a plasma protein and a dispersion of liposome encapsulated hemoglobin; and then (b) subjecting the solution to a force sufficient to reduce the median size of the liposomes to less then 0.2 μm wherein the resulting liposomes are unilamellar and have a unimodal particle size distribution.

DETAILED DESCRIPTION OF THE INVENTION

The preferred process of the present invention is initiated with the formation of a powder or film containing a neutral lipid, cholesterol, and a negatively charged lipid. Alpha tocopherol is a preferred ingredient. Neutral lipids suitable for use include egg phosphatidylcholine, distearoyl phosphatidylcholine (DSPC), hydrogenated soy choline (HSPC), dimyristoylphosphatidylcholine (DMPC), hydrogenated egg phosphatidylcholine (HEPC), and dipalmitoylphosphatidylcholine. The preferred neutral lipids have carbon chain lengths from $C_{16}$–$C_{18}$. The preferred neutral lipid is DSPC. The negative lipids include hydrogenated soy phosphatidylglycerol (HSPG), hydrogenated egg phosphatidylglycerol (HEPG), distearyolphosphatidylglycerol (DSPG), dimyristoyl phosphatidylglycerol (DMPG), and dilaurylphosphatidylglycerol (DLPG). The preferred negatively charged lipid is DMPG. The lipid film or powder is provided containing a 100 mg/ml of lipid wherein the formulation contains DSPC:cholesterol:DMPG:α-tocopherol in a molar ratio of 10:9:1:0.4. This general formula is taught in U.S. Pat. No. 4,911,929 to Farmer. It is disclosed in Farmer that the neutral lipid is approximately 50% of the total lipid; the negatively charged lipid is approximately 10% of the total lipid and cholesterol is approximately 40% of the total lipid; and the α tocopherol is approximately 2% of the total lipid.

The powder or film is hydrated in a 120 mg/ml hemoglobin solution dispersed in a 9% sucrose solution. Other sugars such as lactose may be used. Although the preferred embodiment of the invention is carried out having no phosphate buffer, the invention can be carried out using pH 7.4 phosphate buffer. The lipids are hydrated for 30 minutes at 0°–5° C. Multilamellar vesicles formed and dispersed in the solution are passed through a homogenizer under a pressure of 4000 psi at 20°–25° C. The homogenization is preferably carried out using 12–16 passes. The resulting solution is ultrafiltered to remove and recover unencapsulated hemoglobin. An aliquot of 250 mg/ml human serum albumin is added to the solution to bring the bulk concentration of albumin to 10 mg/ml. The solution is then further homogenized under a pressure of 4000 psi at 20°–25° C., again using 12–16 passes. An additional aliquot of 250 mg/ml human serum albumin is added to the solution to bring the bulk concentration of albumin to 20 mg/ml. The solution is further homogenized at the same pressure and temperature for 6 passes. The solution is ultrafiltered to remove the unencapsulated hemoglobin and human serum albumin. This step occurs with a buffer exchange in which 2–3.7 mg/ml human albumin is provided in a buffer. The solution is then put through a series of filtration steps end with the use of a 0.45 micron filter and 0.2 micron filter to provide for a sterile solution of liposome encapsulated hemoglobin suitable for liquid storage at 4° or lyophilization.

Although human hemoglobin has been used for the present invention, other sources of hemoglobin including recombinant hemoglobin or bovine/porcine hemoglobin may also be used. This procedure results in liposome encapsulated hemoglobin having a median size of 0.09 to 0.15 μm wherein the particle size distribution is normally displayed having a greater then 80% mean volume. The present invention also provides for a particle size distribution having 100% volume in a unimodal distribution. Although the preferred solution is carded out in 9% sucrose without phosphate, phosphate buffer may be used in a general range of pH is 6.8–8.0. The preferred embodiment also discloses an initial application of a force, e.g. a homogenizer with 12–16 passes, prior to the addition a human serum albumin. However, with solutions less than 20–30 mM phosphate buffer the albumin may be added prior to the initial application of force. In all cases a second application of energy sufficient to reduce the size of the liposomes is necessary once the albumin is added to the solution. The preferred buffer solution contains less then 20 mM phosphate. The preferred concentration of human albumin during homogenization is from 10–30 mg/ml, although a concentration of 20 mg/ml is preferred. It is also necessary to maintain a concentration of human albumin at concentration greater than or equal to 2 mg/ml in the ultrafilter buffers during ultrafiltration to prevent reaggregation. It is also desirable to bring the final product albumin concentration to 3.7 mg/ml to mimic physiological conditions. The preferred range of concentration of starting solution hemoglobin is 75 to 185 mg/ml and the desired preferred range is 120 mg/ml. While I do not wish to be bound to any particular therapy, it appears that the addition of a plasma protein such as human serum albumin, and those proteins which are "C-Shaped" and possess a hydrophobic pocket, might be able to "coat" sites of unencapsulated or denatured hemoglobin residing on the surface of the liposomes when added in conjunction with the application of a force necessary to reduce the size of the liposome, and thus disrupt the tendency toward aggregation. The concepts noted herein are also suitable for other formulations having a surface accessible or surface associated active ingredient.

It is known in the art that hyperosmotic saline or other hyperosmotic (with respect to human blood) solutions are not suitable for forming a stable liposomal product. Previous studies in our laboratories have shown that without the addition of a protein such as albumin as disclosed herein, liposome encapsulated hemoglobin dispersions irreversibly aggregate. The aggregation after sonication or homogenization was characterized by a particle size distribution having a broad multimodal distribution with two main size populations. The population of liposomes having a median size less than 0.2 μm was generally less than 60 percent by volume as measured by laser light scattering methods. The first population was approximately 0.1 to 0.15 μm in size and a second population was approximately 1 to 2 microns in median diameter. FIG. 1 is illustrative of a liposome encapsulated hemoglobin formulation homogenized in the absence of saline and in the presence of a 9% sucrose solution. It was determined that this aggregation was irreversible due to the inability of workers to observe a decrease in aggregation after the application of energy such as heat or bath sonication. The aggregated formulations were not ultra- or sterile filterable.

The use of albumin in liposome formulations for other purposes is known. For example, ox albumin is added to a colloidal dispersion of liposomes as a stabilizer during dehydration in U.S. Pat. No. 4,229,360. Proteins, and in particular bovine albumin, have been disclosed as suitable for use as a cryoprotectant in WO 90/03795. U.S. Pat. No. 4,746,516 discloses the lyophilization of liposomes in the presence of hydrophilic excipients, including albumin.

The general idea of the use of albumin, a physiologically acceptable excipient, to prevent aggregation in liposome dispersions was first investigated by the addition of albumin after liposome formation (that is, after the application of the liposome forming force) and before or during filtration. Albumin was introduced into a solution containing a dispersion of liposome encapsulated hemoglobin via a dialysis/ultrafiltration system at two concentrations (1% and 5%). The ultrafiltration step initially commenced at 10% albumin and 5% albumin, but pressure increases during processing of the 10% lot forced dilution to 1%. The addition of albumin to the external phase of the liposomes did not result in the prevention of post homogenization aggregation.

This invention will be more fully understood by reference to the following examples, which are not intended to be limiting but are illustrative of the invention.

EXAMPLE 1

Liposome encapsulated hemoglobin samples were prepared as follows. Distearoyl phosphatidylcholine, cholesterol, dimyristoylphosphatidylglycerol, and α-tocopherol in a molar ration of 10:9:1:0.4 were dissolved in chloroform and methanol (1:1 by volume). The resulting solution was stirred and gently heated until the lipids completely dissolved. A lipid powder was obtained ming a standard spray drying procedure wherein the spraying took place under nitrogen at a temperature of 45° C. The lipid powder was collected and combined with a solution of 120 mg/ml hemoglobin dispersed in an aqueous solution of 9% sucrose and 50 mM phosphate buffer (pH 7.4). The concentration of the lipids in the solution was 100 mg/ml. The solution was mixed with a laboratory mixer (speed=4–6) at 0°–5° C. for 30 minutes. The mixed solution was placed in a modified Gaulin homogenizer for at least 30 passes through the homogenizing valve. Three samples were obtained at three intervals in the process. The first was removed from the process prior to the application of the homogenization force, the second was removed from the process after 15 passes through the homogenizing valve and the third was removed after 30 passes through the homogenizing valve and subsequent ultrafiltration to remove unencapsulated hemoglobin. Each sample was diluted 1:1 in 9% sucrose, 30 mM phosphate buffer and split into thirds. For each sample, a control was used—no albumin was added. Another aliquot was mixed (vortex mixing and/or bath sonication) with an aliquot of human serum albumin (HSA) sufficient to yield a concentration of 10 mg/ml of albumin and a third aliquot was mixed with the same amount of albumin as the second aliquot but a force was applied using a Sonics and Materials Vibra Cell Sonicator for three-four minute intervals, cooling the probe tip in an ice bath between sonication. The results for samples 1, 2 and 3 are shown in Tables 1, 2 and 3 respectively.

TABLE 1

POST HYDRATION + HSA

| HSA | Peak Number | Median Diameter (μm) | Volume % |
|---|---|---|---|
| None | 1 | 1.8748 | 100 |
| Mixed Only | 1 | 0.9845 | 100 |
| Probe Sonicated | 1 | 0.8115 | 81 |
| | 2 | 0.0849 | 19 |

TABLE 2

PASS 15 + HSA

| HSA | Peak Number | Median Diameter (μm) | Volume % |
|---|---|---|---|
| None | 1 | 2.3977 | 8 |
| | 2 | 0.4225 | 29 |
| | 3 | 0.1166 | 63 |
| Mixed Only | 1 | 1.8568 | 16 |
| | 2 | 0.5573 | 29 |
| | 3 | 0.1303 | 55 |
| Probe Sonicated | 1 | 2.2586 | 15 |
| | 2 | 0.111 | 85 |

TABLE 3

POST ULTRAFILTRATION + HSA

| HSA | Peak Number | Median Diameter (μm) | Volume % |
|---|---|---|---|
| None | 1 | 1.6023 | 34 |
| | 2 | 0.1311 | 66 |
| Mixed Only | 1 | 1.4514 | 46 |
| | 2 | 0.1412 | 54 |
| Probe Sonicated | 1 | 0.8878 | 18 |
| | 2 | 0.1033 | 82 |

All the control samples displayed multimodal or very large (greater than or equal to one micron) size distributions not suitable for 0.45 or 0.22 micron filtration. Similarly, the two post hydration samples that did not have any force applied contained only large particles approximately 1 to 2 microns in diameter. Each of the samples that were mixed with albumin (without the application of a force) did not show any improvement in the particle size distribution and were unsuitable for 0.45 or 0.22 micron filtration. This was true for samples taken at post hydration, post pass 15 and post pass 30 with ultrafiltration. The post hydration sample sonicated with albumin contained only 19% of liposome particles in the desired range of approximately 100 nm, suggesting that at this phosphate concentration, albumin added prior to the application of the force sufficient to reduce the size of liposomes did not decrease aggregation. In fact, this sample had a less deskable particle size distribution than samples prepared in the absence of albumin.

The samples probe sonicated in the presence of albumin after they were passed through the homogenizer increased the populations of liposomes in the approximately 100 nm range peak to 82% and 85% as shown in Tables 2 and 3. The samples that were removed after pass 15 and probe sonicated with albumin were successfully filtered through a set of 0.8, 0.45 and 0.2 micron (PVDF filters) series (the particle size of LEH was generally equal to 113.0 nm median diameter post filtration). The resulting liposome encapsulated hemoglobin was purified from unencapsulated hemoglobin on a Sephacryl S-300 column eluted with 9% sucrose and 30 mM phosphate, pH 7.4. The liposome fraction was collected and filtered through a tandem series of PVDF filters 0.8, 0.45 and 0.22 microns yielding a preparation with a median diameter of 115.5 nm.

EXAMPLE 2

Liposomes were prepared as in Example 1 except that they were hydrated in either a 9% sucrose, 30 mM pH 7.4 phosphate buffer or in 9% sucrose, pH 7.4, 0.0 mM phosphate buffer. Aliquots (5 ml) were removed from the 30 mM phosphate samples after passes 1, 3, 5, 10, 15, 20, 25 and 30 through the homogenizing valve. The 5 ml aliquots for the 0.0 mM phosphate buffer were removed after passes 1, 15 and 30 through the homogenizing valve. An aliquot of albumin was added to each sample to bring the sample concentration of albumin up to 10 mg/ml. A force was applied to each sample (Sonics and Materials Vibra Cell Sonicator) for two 4 minute intervals (cooling the probe tip in an ice bath between sonication at 20%, duty cycle, output equal to 3, in an ice bath at a temperature of 0°–5° C.). Particle size was measured after a second aliquot of albumin (to yield a total sample concentration of 20 mg/ml albumin) was added and shear force was applied as described above. Size measurements were determined using a Micro Trac laser light scattering instrument. The results obtained for the zero phosphate samples prepared and removed after one pass, when albumin is added, displayed a majority of liposomes (mean volume greater than 90%), having a median size of from 90 nm to 121 nm. Most of these samples displayed a unimodal particle size distribution with a mean volume of 100%. The preferred results were obtained after the addition of the two aliquots of human serum of albumin each time followed by brief probe sonication. Samples removed at pass 1, 15, or 30 all yielded liposome encapsulated hemoglobin with particle size distribution of 90 to 95 nm median diameter with practically all samples displaying a unimodal particle size distribution with a mean volume of 10%.

Samples prepared in 30 mM phosphate buffer tend to have approximately 95% of the distribution by volume with a median diameter of 80 to 90 nm after more passes (>3).

EXAMPLE 3

This experiment was conducted to determine the effect of buffer strength in producing sterile filterable liposomes having a unimodal particle size distribution when albumin is added prior to the addition of any force sufficient to reduce the size of the liposomes. Multilamellar liposomes were obtained as in example 1 just after hydration) with various phosphate buffer strength and quantity of human serum albumin sufficient to bring the bulk HSA concentration to 10 mg/ml was added to each solution followed by sonication. A second aliquot of human serum sufficient to bring the bulk HSA concentration to 20 mg/ml albumin was then added followed by a second sonication. The particle size was measured. Table 4 summarizes the results. As can be seen at 40 mM phosphate buffer and below, liposome encapsulated hemoglobin dispersed in a solution is formed having a size distribution which is suitable for sterile filtering. The significance of this experiment is that equal to or under the 40 mM phosphate buffer albumin or other plasma proteins may be added to the solution prior to the application of a force sufficient to reduce the size of the liposome.

TABLE 4

ADDITION OF ALBUMIN TO MLV SOLUTIONS OF LEH AT VARIOUS PHOSPHATE CONCENTRATIONS

| | Particle Sizing | | |
|---|---|---|---|
| Phosphate | Peak Number | Median Diameter (μm) | Volume % |
| 0 | 1 | 0.0972 | 100 |
| 1 | 1 | 0.1071 | 100 |
| 5 | 1 | 0.1067 | 100 |
| 10 | 1 | 0.0941 | 100 |
| 20 | 1 | 0.0951 | 100 |
| 30 | 1 | 2.5218 | 4 |
| | 2 | 0.1214 | 96 |
| 40 | 1 | 2.4178 | 17 |
| | 2 | 0.1255 | 83 |
| 50 | 1 | 1.4909 | 48 |
| | 2 | 0.1448 | 52 |

EXAMPLE 4

The following experiment was conducted to identify plasma proteins other than albumin that are suitable to yield non-aggregated filterable liposome encapsulated hemoglobin. A lipid solution was hydrated as in example 1 in a pH 7.4 0 mM aqueous solution (9% sucrose) wherein the samples were removed after one pass through a homogenization valve. Aliquots of either alpha/beta globulin (found in fraction IV plasma protein) or gamma globulin (found in fraction II plasma proteins) were added to separate samples to bring the sample concentration of globulins up to 10 mg/ml. A shear force was applied to each sample for two 4 minute intervals using a Sonics and Materials Vibra Cells Sonicator and cooling the probe tip in ice bath between sonication (At 20° C. duty cycle, output equals 3, in an ice bath). A second aliquot of globulin (to yield a total sample concentration of 20 mg/ml) was added and shear force was applied as described above. The results are summarized in tables 5 and 6.

TABLE 5

SUMMARY OF THE ADDITION OF ALPH/BETA GLOBULINS TO LEH

| | Particle Sizing | | |
|---|---|---|---|
| Alpha/Beta Globulins | Peak Number | Median Diameter (μm) | Volume % |
| None | 1 | 2.2004 | 23 |
| | 2 | 0.6631 | 42 |
| | 3 | 0.1543 | 35 |
| 10 mg/ml + sonication | 1 | 0.8875 | 14 |
| | 2 | 0.1475 | 86 |
| (2) 10 mg/ml + sonication | 1 | 1.1687 | 17 |
| | 2 | 0.1236 | 83 |

TABLE 6

SUMMARY OF THE ADDITION OF GAMMA GLOBULINS TO LEH

| | Particle Sizing* | | |
|---|---|---|---|
| Gamma Globulins | Peak Number | Median Diameter (μm) | Volume % |
| None | 1 | 2.2004 | 23 |
| | 2 | 0.6631 | 42 |
| | 3 | 0.1543 | 35 |
| 10 mg/ml + sonication | 1 | 0.1402 | 100 |
| (2) 10 mg/ml + sonication | 1 | 0.1177 | 100 |

Use of the alpha/beta globulins achieved 83% of the particle distribution residing in the 124 nm main peak, which is a significant improvement of the control value. The particle distribution for the gamma globulins was unimodal with a median diameter of 140 nm after 10 mg/ml was added and remained unimodal and easily filterable after 20 mg/ml was added.

EXAMPLE 5

Various raw material sources were used and compared throughout the process steps in hemoglobin including Letterman Human $A_0$, Letterman diaspifin-crosslinked hemoglobin (DCL-Hb), Somatogen recombinant hemoglobin (rHb 1.1). All samples were processed using albumin. The experiments were carried out as follows. Lipid powder was hydrated for 30 minutes at 0° to 5° C., in 9% sucrose hemoglobin solution with no phosphate. The resulting multilamellar solution of liposomes was then homogenized at 4000 psi, at 20–25 degrees celsius for 12–16 passes. The solution was then ultrafiltered to recover the unencapsulated hemoglobin. An aliquot of human serum albumin was added sufficient to big the bulk concentration to 10 mg/ml. The solution was again homogenized at 4000 psi, at 20–25 degrees celsius for the 12–16 passes. A second aliquot of human serum albumin was added to bring the bulk concentration to 20 mg/ml, and the sample homogenized again for 6 passes (the results are shown in Table 7).

TABLE 7

| Type of Hb | Median Diameter (μm) | % in Peak |
|---|---|---|
| Letterman Ao | 0.1042 | 100 |
| Letterman Ao | 0.1430 | 100 |
| Somatogen rHb 1.1 | 0.1446 | 100 |
| Somatogen rHb 1.1 | 0.1276 | 100 |
| Somatgen rHb 1.1 | 0.1459 | 88 |
| Letterman DCL-Hb | 0.1276 | 100 |

EXAMPLE 6

Animal toxicity studies were conducted to assess the potential antigenicity of albumin as used in the process. Female Balb-c mice were injected with a solution of liposome encapsulated hemoglobin prepared with albumin and compared to empty (no hemoglobin) liposome encapsulated hemoglobin prepared with albumin and 9% sucrose with albumin. No toxicities were noted or deaths encountered in any of the preparations.

The foregoing description is intended to present the preferred embodiments that may be utilized in practicing the present invention, but it will be apparent to those skilled in the art that modifications and equivalents may be incorporated without departing from the scope and spirit of the invention.

I claim:
1. A process for producing a non-aggregating dispersion of liposomes, comprising:
   a) forming a dispersion of preformed liposomes containing an active therapeutic or an imaging agent;
   b) adding a solution of a globular protein to the dispersion;
   c) then subjecting the dispersion to a force sufficient to reduce the median size of the liposomes to less than 0.2 μm wherein the resulting liposomes are unilamellar, provided that when the globular protein is added prior to an initial application of force the dispersion comprises an aqueous solution having an ionic strength of below 50 mM; and
   d) filtering the resulting liposomes through a filter having a size less than or equal to 0.45 μm,
   wherein the protein is selected from the group consisting of albumin, immunoglobulin, alpha, beta or gamma globulin, a lipoprotein and mixtures thereof.

2. The process of claim 1 wherein the protein is albumin.
3. The process of claim 1 wherein the liposomes have a median diameter of less that 0.15 μm.
4. The process of claim 2 wherein the liposomes have a median diameter of less that 0.15 μm.

* * * * *